United States Patent [19]
Cordier et al.

[11] Patent Number: 5,202,468
[45] Date of Patent: Apr. 13, 1993

[54] PROCESS FOR PRODUCING METHYL ACETATE FROM METHYL FORMATE

[75] Inventors: Jean A. Cordier, St. Saulve; Francis P. Petit; Yves Castanet, both of Villeneuve d'Asq; Serge Melloul, Paris; André Mortreux, Hem, all of France

[73] Assignee: Sollac, Puteaux, France

[21] Appl. No.: 896,721

[22] Filed: Jun. 9, 1992

Related U.S. Application Data

[63] Continuation of Ser. No. 776,687, Oct. 15, 1991, filed as PCT/FR89/00195, Apr. 24, 1989, abandoned, which is a continuation of Ser. No. 460,325, Feb. 22, 1990, abandoned.

[30] Foreign Application Priority Data

Apr. 25, 1988 [FR] France .................. 8805462

[51] Int. Cl.$^5$ ............... C07C 67/00; C07C 67/02; C07C 69/00
[52] U.S. Cl. .................................................. 560/265
[58] Field of Search ........................................ 560/265

[56] References Cited

U.S. PATENT DOCUMENTS 4,853,482  8/1989  Drury .................................. 562/607

FOREIGN PATENT DOCUMENTS 50-16773  6/1975  Japan .
1286224  8/1972  United Kingdom ................ 562/607

Primary Examiner—Arthur C. Prescott
Attorney, Agent, or Firm—Oblon, Spivak, McClelland, Maier & Neustadt

[57] ABSTRACT

The object of the invention is a process for the preparation of methyl acetate starting from the methyl formate, characterized in that methyl formate is converted at a temperature of 170° to 220° C. in the presence of:
a) a catalyst based on rhodium,
b) an iodine-containing promoter selected from among the alkaline, alkaline earth, phosphonium or ammonium iodides and the mixtures of covalent compounds of iodine supplemented with a phosphine or a tertiary amine.
c) a solvent selected from a cyclic N-alkyl amide.

11 Claims, No Drawings

PROCESS FOR PRODUCING METHYL ACETATE FROM METHYL FORMATE

This application is a continuation of application Ser. No. 07/776,687, filed on Oct. 15, 1991, filed as PCT/FR89/00195, Apr. 24, 1989, now abandoned, which is a continuation of U.S. Ser. No. 07/460,325, filed Feb. 22, 1990, now abandoned.

The present invention relates to a process for the selective preparation of methyl acetate starting from methyl formate.

The isomerization of methyl formate to acetic acid according to the following scheme is a well-known reaction.

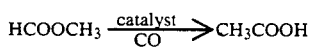
$$HCOOCH_3 \xrightarrow[CO]{catalyst} CH_3COOH$$

In the liquid phase, it is catalysed by numerous transition metals of group VIII, among which iridium, rhodium, cobalt, ruthenium and palladium are the most often cited in the literature. The reaction is usually carried out in the presence of an iodine-containing promoter ($CH_3I$, $HI$), at a temperature varying between 150° and 200° C. and most often under a pressure of carbon monoxide, the role of which consists uniquely in stabilizing the catalytic species.

The selectivity towards acetic acid, which may be good (99%), depends on the experimental conditions: catalysts, solvent, promoter, co-catalyst . . . .

The influence of these various parameters has been studied by Röper et al. (Erdöl und Kohle, Erdgas Petrochem., 38 (1), 1985), the principal by-product always being methyl acetate which is formed in appreciable proportions essentially when the activity of the catalytic system is low (rate of the cycle less than 20 $h^{-1}$).

The present invention aims to provide a process for the synthesis of methyl acetate having a good selectivity starting from methyl formate. The reactions which may be involved are the following:

$$2HCOOCH_3 \xrightarrow{catalyst} CH_3COOCH_3 + HCOOH$$

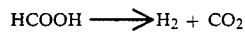
$$HCOOH \longrightarrow H_2 + CO_2$$

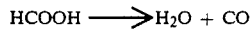
$$HCOOH \longrightarrow H_2O + CO$$

Thus, under the conditions or the reaction, the formic acid initially co-produced is decomposed to give CO, hydrogen, $CO_2$ and water.

The invention is characterized in that methyl formate is made to react at a temperature of 170° to 220° C. in the presence of:
a) a catalyst based on rhodium,
b) an iodine-containing promoter selected from among the alkaline, alkaline earth, phosphonium and ammonium iodides and the covalent compounds of iodine supplemented with a phosphine or a tertiary amine, this promoter being present in a molar concentration of 0.05 to 1 mole/liter,
c) a solvent selected from a cyclic N-alkyl amide.

As an example of a catalyst based on rhodium mention may be made of $RhCl_3, 3H_2O$—$RhCl_2(CO)_4$ or $Rh(CO)Cl(PPh_3)_2$.

The iodine-containing promoter is preferably an alkaline or alkaline earth iodide such as LiI, NaI, KI, $CaI_2$.
. . .

It may also possibly be covalent: $I_2$, $CH_3I$, $HI$ . . . . In this case, the addition of a phosphine $PR_3$ or a tertiary amine $NR_3$ (R being an alkyl or aryl group, in particular $PPh_3$) in a ratio of 1 to 2 with the promoter proves to be beneficial.

The solvent is advantageously used in a molar proportion of 10 to 50% with respect to the formate. As an example of a cyclic N-($C_1$-$C_6$ alkyl) amide mention may be made of N-methylpyrrolidone, N-ethylpyrrolidone and N,N-dimethylimidazolidinone.

The reaction may be carried out without an initial pressure of CO. It is, however, advantageous to work under a pressure of CO included between $1.10^5$ and $20.10^5$ Pa, in particular in order to avoid the decomposition of the formate into CO and methanol and to improve the selectivity towards methyl acetate. Higher pressures are also possible but most often result in a fall in activity.

The catalyst is advantageously used in molar proportion included between $10^{-3}$ and $4.10^{-4}$.

The following examples illustrate the process of the invention:

EXAMPLE 1

1 g of LiI in solution in 30 $cm^3$ of methyl formate and 10 $cm^3$ of N-methylpyrrolidone (NMP) are introduced into a 100 $cm^3$ autoclave. The autoclave is purged by a current of CO, then pressurised to $5.10^5$ Pa. Then it is heated to 180° C. with stirring; when the temperature has stabilized, 0.06 g of $RhCl_3$, $3H_2O$ dissolved in 10 $cm^3$ of NMP is injected rapidly (2 minutes) with a dosing pump. The conversion of the methyl formate is monitored by the gas chromatographic analysis of periodic samples, the end of the injection of the catalyst being taken as time zero. At the end of 4 hours of reaction the stirring is stopped, the autoclave is cooled, the gas and liquid phases are analysed by chromatography.

| Results: | |
|---|---|
| Concentration in the liquid phase (molar %) | Concentration in the gas phase (molar %) |
| MeOMe = 1.2 | $H_2$ = 2 |
| MeOH = 1.7 | CO = 48 |
| $HCOOCH_3$ = 78 | $CO_2$ = 34 |
| $CH_3COOCH_3$ = 18.3 | $CH_4$ = 16 |

The kinetic results obtained in Example 1 are presented in Table I, as well as other results obtained by utilizing an experimental protocol similar to that described in Example 1.

TABLE 1

| Expt. No. | Exptl. conditions | t (h) | % total conversion | % molar selectivities in terms of methyl acetate | cycle rate ($h^{-1}$) |
|---|---|---|---|---|---|
| 1 | $RhCl_3.3H_2O$ = 0.25 mmole | 0.1 | 8.7 | 53 | |
| | LiI = 1 g | 0.25 | 21 | 94.2 | 1680 |
| | FOMe = 500 mmoles | 1 | 24.8 | 94.4 | 496 |
| | NMP = 20 $cm^3$ T = 180° C. PCO = 1 MPa | 3 | 28.4 | 91.5 | 189 |
| 2 | $RhCl_3.3H_2O$ = 0.25 mmole | 1.25 | 4.8 | 39.6 | |

TABLE 1-continued

| Expt. No. | Exptl. conditions | t (h) | % total conversion | % molar selectivities in terms of methyl acetate | cycle rate (h$^{-1}$) |
|---|---|---|---|---|---|
|  | ICH$_3$ = 1 g | 2.5 | 11.3 | 83.2 | 90 |
|  | PPh$_3$ = 1 g | 4.5 | 16.8 | 73.7 | 75 |
|  | FOMe = 500 mmoles |  |  |  |  |
|  | NMP = 20 cm$^3$ |  |  |  |  |
|  | T = 180° C. |  |  |  |  |
|  | PCO = 1 MPa |  |  |  |  |
| 3 | RhCl$_3$.3H$_2$O = 0.25 mmole | 0.5 | 17.9 | 75 | 716 |
|  | LiI = 0.15 g | 1 | 26 | 85.8 | 520 |
|  | ICH$_3$ = 1 g | 2 | 33.5 | 92.5 | 325 |
|  | FOMe = 500 mmoles | 3 | 36.8 | 92.7 | 245 |
|  | NMP = 20 cm$^3$ |  |  |  |  |
|  | T = 180° C. |  |  |  |  |
|  | PCO = 1.5 MPa |  |  |  |  |
| 4 | RhCl$_3$.3H$_2$O = 0.125 mmole | 0.5 | 15.6 | 79.5 | 414 |
|  | LiI = 1.5 g | 1 | 34.8 | 81.6 | 462 |
|  | NMP = 20 cm$^3$ | 2.5 | 39.1 | 84.6 | 207 |
|  | FOMe = 166 mmoles |  |  |  |  |
|  | T = 180° C. |  |  |  |  |
|  | PCO = 5 MPa |  |  |  |  |
| 5 | RhCl$_3$.3H$_2$O = 0.15 mmole | 1.5 | 34 | 93.3 | 373 |
|  | LiI = 2 g | 2.5 | 71.1 | 80.4 | 468 |
|  | FOMe = 245 mmoles | 3.5 | 92 | 50.1 | 432 |
|  | NMP = 15 cm$^3$ |  |  |  |  |
|  | T = 196° C. |  |  |  |  |
|  | PCO = 10 MPa |  |  |  |  |
| 6 | RhCl$_3$.3H$_2$O = 0.15 mmole | 3.5 | 34.5 | 81.7 | 162 |
|  | LiI = 1 g | 4.5 | 52 | 80.3 | 190 |
|  | FOMe = 247 mmoles | 5.5 | 72.6 | 71.9 | 217 |
|  | NMP = 15 cm$^3$ |  |  |  |  |
|  | T = 196° C. |  |  |  |  |
|  | PCO = 30 MPa |  |  |  |  |
| 7 | RhCl$_3$.3H$_2$O = 0.15 mmole | 3 | 71.7 | 92.5 | 393 |
|  | LiI = 0.25 g | 4 | 81.9 | 90.6 | 337 |
|  | FOMe = 247 mmoles | 5 | 88.5 | 81.4 | 291 |
|  | NMP = 15 cm$^3$ |  |  |  |  |
|  | T = 196° C. |  |  |  |  |
|  | PCO = 30 MPa |  |  |  |  |

FOMe = methyl formate
NMP = N-methylpyrrolidone

EXAMPLE 8

One proceeded as in Example 1 but in utilizing 0.065 mmole of catalyst RhCl$_3$, 3H$_2$O, 180 mmole of methyl formate, 50 cm$^3$ of solvent NMP at a temperature of 184° C. under a CO pressure of 5 MPa. The amount of iodine-containing promoter LiI was made to vary and the percentage conversion into methyl acetate and the selectivity were determined at the end of 2 h.

| promoter catalyst ratio | % conversion into methyl acetate | % selectivity in terms of methyl acetate |
|---|---|---|
| 40 | 5 | 14 |
| 100 | 30 | 70 |
| 200 | 30 | 84 |

EXAMPLE 9

By way of comparison, one proceeded as in Example 1 but in utilizing 1.3 mmole of RhCl$_3$, 3H$_2$O; 820 mmoles of methyl formate without solvent at 180° C. and 20 MPa of CO. Practically only acetic acid is obtained, which shows clearly the influence of the solvent.

| Experimental conditions | t (h) | % total conversion | % molar selectivity in terms methyl acetate | % molar selectivity in terms of acetic acid |
|---|---|---|---|---|
| RhCl$_3$.3H$_2$O = 1.30 mmoles | 1 | 72 | 2.2 | 97.9 |
| LiI = 2.8 g |  |  |  |  |
| FCMe = 820 mmoles | 2 | 96.5 | 0.5 | 99.5 |
| T = 180° C. |  |  |  |  |
| P = 20 MPa | 3 | 99.3 | 0.3 | 99.7 |

We claim:

1. A process for the preparation of methyl acetate starting from methyl formate, comprising the step of converting methyl formate to methyl acetate with good selectivity at a temperature of 170° to 220° C. in the presence of
   a) a catalytically effective amount of a catalyst based on rhodium,
   b) an iodine-containing promoter selected from alkaline iodides, alkaline earth iodides, phosphonium iodides, ammonium iodides, and the covalent compounds of iodine supplemented with a phosphine or a tertiary amine in a ratio of 1 to 2 with said promoter, this promoter being present in a molar concentration of 0.05 to 1 mole/liter, and
   c) a solvent selected from cyclic N-alkyl amides.

2. A process for the preparation of methyl acetate starting from methyl formate, comprising the step of converting methyl formate to methyl acetate with good selectivity at a temperature of 170° to 20° C. in the presence of a catalyst based on rhodium; a promoter comprising an alkaline iodide or an alkaline earth iodide, this promoter being present in a molar concentration of 0.05 to 1 mole/liter; and a solvent selected from a cyclic N-alkyl amide.

3. A process according to claim 1, characterized in that the promoter is a covalent compound of iodine in a mixture with a tertiary amine.

4. A process according to claim 1, characterized in that the promoter is a covalent compound of iodine in a mixture with a phosphine.

5. A process according to claim 1, characterized in that the solvent is utilized in a molar proportion of 10 to 50% with respect to the methyl formate.

6. A process according to claim 1, characterized in that one works under a CO pressure of $1.50^5$ to $20.10^5$ Pa.

7. A process for the catalytic preparation of methyl acetate from methyl formate, comprising:
   contacting in a cyclic N-alkyl amide solvent and at a temperature of from 170° C. to 220° C., methyl formate, a rhodium-based catalyst present in a catalyst effective amount, and iodide ions present in a promoter effective amount; and
   obtaining methyl acetate with good selectivity.

8. The process of claim 7, wherein said iodide ions are present in an amount of from 0.05 to 1 mole/liter.

9. The process of claim 7, wherein said rhodium-based catalyst is present in an amount of from $10^{-3}$ to $4 \times 10^{-4}$ M.

10. The process of claim 7, wherein said cyclic N-alkyl amide is a cyclic N-(C$_{1-6}$ alkyl) amide.

11. The process of claim 7, wherein said cyclic N-alkyl amide is N-methylpyrrolidone, N-ethylpyrrolidone or N,N-dimethylimidazolidinone.

* * * * *